United States Patent
Chin, Jr. et al.

(10) Patent No.: US 8,449,442 B2
(45) Date of Patent: May 28, 2013

(54) METHOD AND DEVICE FOR PERCUTANEOUS LEFT VENTRICULAR RECONSTRUCTION

(75) Inventors: Sing-Fatt Chin, Jr., Fremont, CA (US); Arthur Bertolero, Danville, CA (US); Lon S. Annest, Tacoma, WA (US)

(73) Assignee: BioVentrix, Inc., San Ramon, CA (US)

( * ) Notice: Subject to any disclaimer, the term of this patent is extended or adjusted under 35 U.S.C. 154(b) by 299 days.

(21) Appl. No.: 11/961,990

(22) Filed: Dec. 20, 2007

(65) Prior Publication Data

US 2008/0097148 A1    Apr. 24, 2008

Related U.S. Application Data

(63) Continuation of application No. 11/248,521, filed on Oct. 12, 2005, now abandoned.

(60) Provisional application No. 60/618,835, filed on Oct. 13, 2004.

(51) Int. Cl.
*A61F 2/00* (2006.01)

(52) U.S. Cl.
USPC ............... 600/16; 600/37; 607/116; 607/129

(58) Field of Classification Search
USPC ................... 600/16, 17, 18, 37; 607/116, 129
See application file for complete search history.

(56) References Cited

U.S. PATENT DOCUMENTS

| | | | |
|---|---|---|---|
| 4,007,743 A | 2/1977 | Blake | |
| 5,295,958 A | 3/1994 | Shturman | |
| 5,830,224 A | 11/1998 | Cohn et al. | |
| 5,961,440 A | 10/1999 | Schweich, Jr. et al. | |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,125,852 A | 10/2000 | Stevens et al. | |
| 6,162,168 A | 12/2000 | Schweich, Jr. et al. | |
| 6,165,119 A | 12/2000 | Schweich, Jr. et al. | |
| 6,166,684 A | 12/2000 | Yoshikawa et al. | |
| 6,258,021 B1 | 7/2001 | Wilk | |
| 6,260,552 B1 | 7/2001 | Mortier et al. | |
| 6,406,420 B1 * | 6/2002 | McCarthy et al. | 600/16 |
| 6,494,825 B1 | 12/2002 | Talpade | |

(Continued)

FOREIGN PATENT DOCUMENTS

| | | |
|---|---|---|
| EP | 1 078 644 A1 | 2/2001 |
| WO | WO 00/06028 A1 | 2/2000 |
| WO | WO 02/30335 A2 | 4/2002 |
| WO | 2007/022519 A2 | 2/2007 |

OTHER PUBLICATIONS

European Examination Report of EP Patent Application 05810316.9, dated Mar. 10, 2009, 6 pages total.

(Continued)

*Primary Examiner* — Joseph Stoklosa

(74) *Attorney, Agent, or Firm* — Kilpatrick Townsend & Stockton LLP

(57) ABSTRACT

A method for reducing left ventricular volume, which comprises identifying infarcted tissue during open chest surgery; reducing left ventricle volume while preserving the ventricular apex; and realigning the ventricular apex, such that the realigning step comprises closing the lower or apical portion of said ventricle to achieve appropriate functional contractile geometry of said ventricle in a dyskinetic ventricle of a heart.

10 Claims, 9 Drawing Sheets

U.S. PATENT DOCUMENTS

| | | | |
|---|---|---|---|
| 6,572,529 B2 | 6/2003 | Wilk | |
| 6,616,684 B1 | 9/2003 | Vidlund et al. | |
| 6,709,382 B1 | 3/2004 | Horner | |
| 6,746,471 B2 | 6/2004 | Mortier et al. | |
| 6,776,754 B1 | 8/2004 | Wilk | |
| 6,808,488 B2 | 10/2004 | Mortier | |
| 7,146,225 B2 * | 12/2006 | Guenst et al. | 607/119 |
| 7,753,923 B2 * | 7/2010 | St. Goar et al. | 606/148 |
| 7,766,816 B2 | 8/2010 | Chin et al. | |
| 7,785,248 B2 | 8/2010 | Annest et al. | |
| 8,123,668 B2 | 2/2012 | Annest et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2003/0032979 A1 | 2/2003 | Mortier et al. | |
| 2003/0163165 A1 | 8/2003 | Bornzin et al. | |
| 2003/0166992 A1 | 9/2003 | Schweich, Jr. et al. | |
| 2003/0181951 A1 | 9/2003 | Cates | |
| 2004/0167580 A1 | 8/2004 | Mann et al. | |
| 2004/0225304 A1 | 11/2004 | Vidlund et al. | |
| 2005/0065506 A1 | 3/2005 | Phan | |
| 2005/0096498 A1 | 5/2005 | Houser et al. | |
| 2005/0288613 A1 | 12/2005 | Heil, Jr. | |
| 2006/0135962 A1 | 6/2006 | Kick et al. | |
| 2006/0161040 A1 | 7/2006 | McCarthy et al. | |
| 2006/0161238 A1 * | 7/2006 | Hall | 607/129 |
| 2006/0241340 A1 | 10/2006 | Schroeder et al. | |
| 2006/0247672 A1 | 11/2006 | Vidlund et al. | |
| 2007/0010876 A1 | 1/2007 | Salahieh et al. | |
| 2007/0049971 A1 | 3/2007 | Chin et al. | |
| 2007/0055303 A1 | 3/2007 | Vidlund et al. | |
| 2007/0073274 A1 | 3/2007 | Chin et al. | |
| 2007/0112244 A1 | 5/2007 | McCarthy et al. | |
| 2007/0203503 A1 | 8/2007 | Salahieh et al. | |
| 2008/0294251 A1 | 11/2008 | Annest et al. | |
| 2009/0093670 A1 | 4/2009 | Annest et al. | |
| 2010/0016655 A1 | 1/2010 | Annest et al. | |
| 2010/0268020 A1 | 10/2010 | Chin et al. | |
| 2011/0160750 A1 | 6/2011 | Annest et al. | |
| 2012/0190958 A1 | 7/2012 | Annest et al. | |

OTHER PUBLICATIONS

International Search Report and Written Opinion of PCT Application No. PCT/US06/32663, Jul. 31, 2007, 5 pages.

International Search Report and Written Opinion of PCT Application No. PCT/US2005/036690, mailed Jul. 9, 2007, 6 pages.

International Search Report and Written Opinion of PCT Application No. PCT/US09/51288, mailed Sep. 15, 2009, 9 pages.

international Search Report and Written Opinion of PCT Application No. PCT/US08/64255, mailed Sep. 29, 2008, 17 pages.

International Search Report and Written Opinion of PCT Application No. PCT/US06/22594, mailed Oct. 1, 2008, 9 pages.

International Search Report and Written Opinion of PCT Application No. PCT/US08/78810, mailed Feb. 12, 2009, 11 pages.

* cited by examiner

FIG. 7C
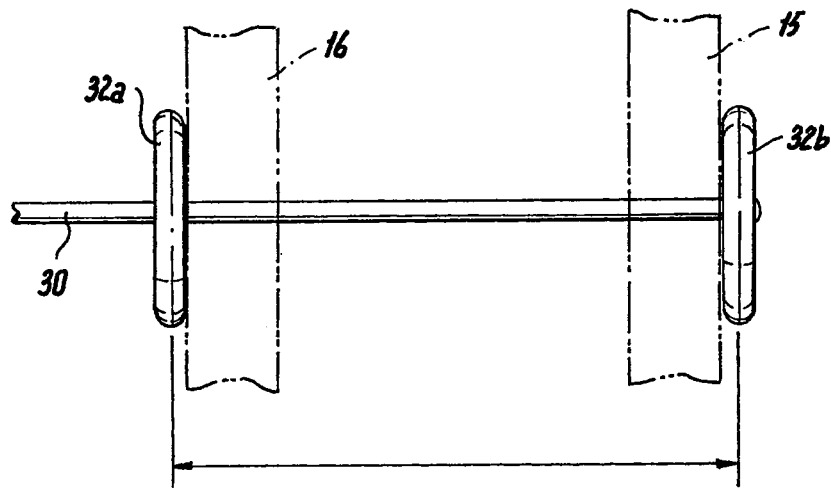
FIG. 7D
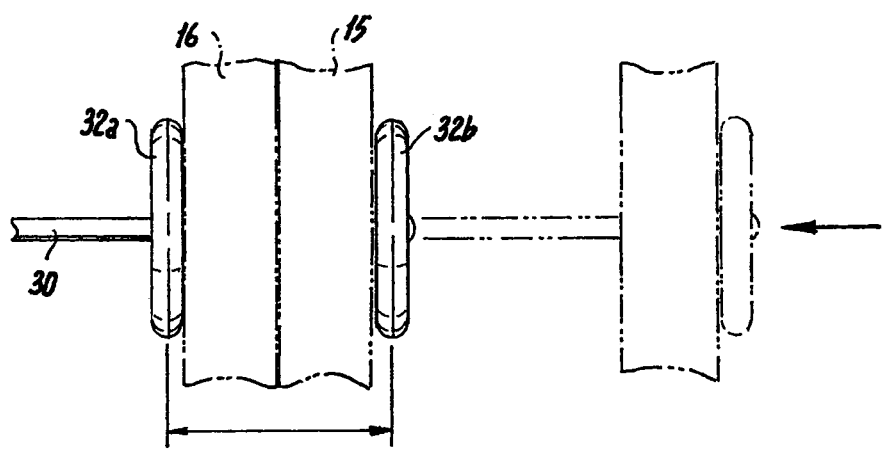
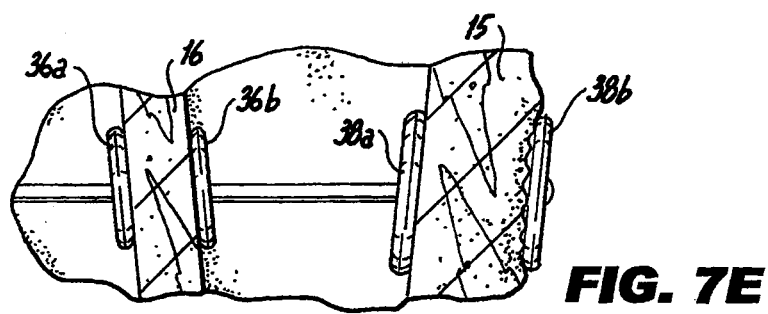
FIG. 7E

METHOD AND DEVICE FOR PERCUTANEOUS LEFT VENTRICULAR RECONSTRUCTION

CROSS-REFERENCES TO RELATED APPLICATIONS

This application is a continuation of U.S. patent application Ser. No. 11/248,521 filed on Oct. 12, 2005, which claims the benefit of under 35 U.S.C. §109(e) of U.S. Provisional Patent Application No. 60/618,835, filed on Oct. 13, 2004, the full disclosures of which are incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

This invention relates to methods and devices for reconstructing the ventricle and for sensing infarcted septum and left ventricle wall during percutaneous left ventricle reconstruction, particularly where there is congestive heart failure.

This invention also relates generally to devices for sizing a ventricle and related methods for positioning the device. More particularly, the invention relates to sizing devices for reducing the ventricular volume to improve the heart's pumping action 2. Description of Related Art Heart failure occurs when the pumping ability of the heart becomes impaired. The term congestive heart failure (CHF) refers to heart failure that is accompanied by congestion of body tissues. Heart failure may be caused by a variety of conditions, including acute myocardial infarction, hypertension, valvular heart disease, or degenerative conditions of the heart muscle known collectively ad cardiomyopathies. Heart failure may exist as either systolic or diastolic (preserved ejection fraction) failure, and right-sided or sided failure. Systolic failure involves a decrease in cardiac contractility and ejection fraction. In systolic heart failure, the ejection fraction declines progressively with increasing degrees of myocardial dysfunction. With a decrease in ejection fraction, there is a resultant increase in diastolic volume, ventricular dilation, ventricular wall tension, and ventricular end-diastolic pressure.

In certain pathological conditions, the ventricles of the heart become ineffective in pumping the blood, causing a back-up of pressure in the vascular system behind the ventricle. The reduced effectiveness of the heart is usually due to an enlargement of the heart. Coronary artery disease causes approximately 60% of congestive heart failure. Acute myocardial infarction (AMI) due to obstruction of a coronary artery is a common initiating event that can lead ultimately to heart failure. A myocardial ischemia may, for example, cause a portion of a myocardium of the heart to lose its ability to contract. Prolonged ischemia can lead to infarction of a portion of the myocardium (heart muscle) wherein the heart muscle dies and become scar tissue. Once this tissue dies, it no longer as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the hearts ability to move blood forward. When local wall motion moves in this way it is said to be dyskinetic. The dyskinetic portion of the myocardium may stretch and eventually form an aneurysmic bulge.

One problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilation is greater than the hypertrophy and the result is a rising wall tension requirement for systolic contraction. This is felt to be an ongoing insult to the muscle myocyte resulting in further muscle damage. In response, the heart tissue remodels to accommodate the chronically increased filling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The increase in wall stress also occurs during diastolic filling. The stress increase requires a larger amount of oxygen supply, which can result in exhaustion of the myocardium leading to a reduced cardiac output of the heart.

Heart failure (HF), the heart's inability to pump an adequate volume of blood to the tissues, is the only major cardiovascular condition that continues to increase in incidence in the United States. Approximate 5 million patients are currently diagnosed with HF in the United States. The American Heart Association estimates that between 400,000 and 700,000 new HF cases develop each year. This condition is responsible for an estimated 900,000 hospitalizations annually—more than any other medical condition among the elderly. Approximately 6.5 million hospital days each year are attributed to and related to HF and as many as one third of those patients are readmitted for treatment of symptom recurrence within 90 days. Thus, it is not surprising that the cost of providing advanced medical care for the millions of patients suffering from HF is extraordinarily high—now estimated at more than $38 billion annually.

In certain pathological conditions, the ventricles of the heart become ineffective in pumping the blood, causing a back-up of pressure in the vascular system behind the ventricle. The reduced effectiveness of the heart is usually due to an enlargement of the heart. Coronary artery disease causes approximately 60% of congestive heart failure. Acute myocardial infarction (AMI) due to obstruction of a coronary artery is a common initiating event that can lead ultimately to heart failure. A myocardial ischemia may, for example, cause a portion of a myocardium of the heart to lose its ability to contract. Prolonged ischemia can lead to infarction of a portion of the myocardium (heart muscle) wherein the heart muscle dies and become scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the hearts ability to move blood forward. When local wall motion moves in this way it is said to be dyskinetic. The dyskinetic portion of the myocardium may stretch and eventually form an aneurysmic bulge.

One problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. In response, the heart tissue remodels to accommodate the chronically increased filling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The increase in wall stress also occurs during diastolic filling. The stress increase requires a larger amount of oxygen supply, which can result in exhaustion of the myocardium leading to a reduced cardiac output of the heart.

Prior treatments for heart failure associated with such dilatation fall into three general categories. The first being pharmacological treatment, for example, diuretics and ACE inhibitors. The second being assist devices, for example, pumps. Finally, surgical treatments also have been experimented with, for example, Dor or Jatene procedure, or left ventricular reconstruction (LVR).

A surgical procedure for reconstruction of the left ventricle, developed by Dr. Vincent Dor, involves surgery via sternotomy by placing the patient on a heart-lung machine. In this operation, the scar tissue is excluded, and a patch is placed where the scar was excluded in order to sculpt the contour of the restored ventricle, and thus, reshape the heart. This results in more efficient contractile function, as the ejection fraction increases and forward output improves. The technique requires open chest surgery (sternotomy or thoracotomy), and is universally considered an invasive procedure. Understandably, the risk, extended recovery period, and discomfort of the sternal incision act as a deterrent to patients and their physicians despite the need to address the disease state for which the procedure is designed.

Hence, it will be beneficial to achieve the desired sizing and shaping of the heart without the highly invasive open chest procedure. A minimally invasive procedure, for example one that is done using a catheter that is inserted into the femoral vein or artery and that accesses the left ventricle, could be highly desirable. Such a procedure shall be able to identify and exclude the infracted tissue, in a way that is comparable to the identification of the infracted tissue is accomplished by simple visualization in an open procedure, and maintain or create the apex that is necessary to recreate the proper functioning of a CHF heart. A proper recreation of the apex of the heart is essential for maintaining effective cardiac contraction.

As mentioned above, the infracted tissue is easily identified during an open chest surgery by visualization. During a closed chest procedure where the heart is accessed using minimally invasive techniques, as contemplated here, it is not possible to visually differentiate the infracted tissue from viable or reversibly-ischemic myocardium. While MRI and nuclear-uptake studies can identify the presence of scar, these are currently not feasible intraoperatively.

Thus, there is a need for sensing infarcted myocardium in the septum from the right or left ventricle, along with a method or device to reduce the left ventricular volume while preserving the apex, and, then to appropriately realign the apex of the left ventricle and alter the geometry and decrease the wall tension in order to improve cardiac ejection fraction).

BRIEF SUMMARY OF THE INVENTION

The present invention describes a method and device to achieve left ventricular volume reduction using minimally invasive surgical techniques by:

1. detecting the appropriate infarcted location in the heart; and
2. reducing left ventricle volume while preserving the apex by realigning the ventricular apex to treat patients with congestive heart failure.

A goal of the present invention is to provide a limited access method for treating congestive heart failure. This is achieved by a minimally invasive technique to reduce left ventricular volume while preserving the apex, and a way of sensing infarcted myocardium (septum and left ventricle wall) to appropriately reconfigure the geometry of the left ventricle and properly align the apex to provide the desired pumping capability of the heart. The present invention may be performed trans-atrially, trans-arterially, or trans-venously, as through femoral vein (percutaneously) with a catheter.

This invention relates to a device and method for treatment of congestive heart failure patients, and particularly to sizing device and method for reducing ventricular volume in patients suffering from congestive heart failure. The device and method may be performed thoracoscopically off-pump which is less expensive and less traumatic to the patient than an open-chest and open-heart surgical technique.

A left ventricular reconstruction typically comprises excluding the infracted tissue. To exclude the infracted tissue, it is important to first locate the tissue to be "excluded". This invention describes a method for identifying infracted tissue while performing left ventricular reconstruction using minimally invasive procedures. Such sensing techniques may include (but are not limited to), (1) pacing (infracted tissue has minimum or no electrical conduction), (2) angiography, (3) echocardiography, and (4) tissue Doppler.

In yet another embodiment, this invention describes a method for performing minimally invasive left ventricular volume reduction in a congestive heart failure heart using a catheter by (a) accessing septum of the heart through the right ventricle; (b) identifying infracted tissue in the septum; (c) advancing the catheter through the infracted tissue of the septum; (d) identifying infracted tissue on the left ventricle wall; (e) bringing together the infracted tissue of the left ventricle and the septum, thereby minimizing the volume of the left ventricle; and (f) recreating an apex of the heart such that the procedure results in the desired geometric configuration and ejection fraction.

Once the boundaries of the scar have been defined using a sensing technique, achieving the clinical goal is dependent on realignment of the apical spatial relationships, and a decrease in the size of the left ventricle to improve ejection fraction and stroke volume. In the process, this invention will diminish wall tension, and therefore oxygen consumption, as well as solving potential alignment disparities by repositioning the apex to an appropriate anatomical configuration.

Another embodiment of this invention comprises a catheter-based, minimally invasive procedure of introducing a catheter into the right ventricle of the heart, via the septum, and into the left ventricle to reduce the volume of the left ventricle while preserving the apex of the left ventricle. This method comprises performing minimally invasive left ventricular volume reduction in a congestive heart failure heart using a catheter by (a) accessing septum of the heart through the right ventricle; (b) identifying tissue in the septum; (c) advancing the catheter through the infarcted tissue of the septum; (d) identifying infracted tissue on the left ventricular wall; and (e) bringing the infracted tissue of the left ventricle and the septum closer to each other and thereby minimizing the volume of the left ventricle.

Another aspect of the present invention pertains to suturing device, and related suturing methods, for thoracoscopy device placement on the heart. The sutures of the present inventions may be placed thoracoscopically. The inventive techniques and devices are thus minimally invasive and less risky to patients.

BRIEF DESCRIPTION OF THE DRAWINGS

The present invention has other advantages and features which will be more readily apparent from the following detailed description of the invention and the appended claims, when taken in conjunction with the accompanying drawings, in which:

FIGS. 7A through 7E illustrate implantable devices in accordance with the present invention for use during percutaneous LVR to bring together the infarcted tissue of the septum and the left ventricular wall.

DETAILED DESCRIPTION OF THE INVENTION

Figure 1A:
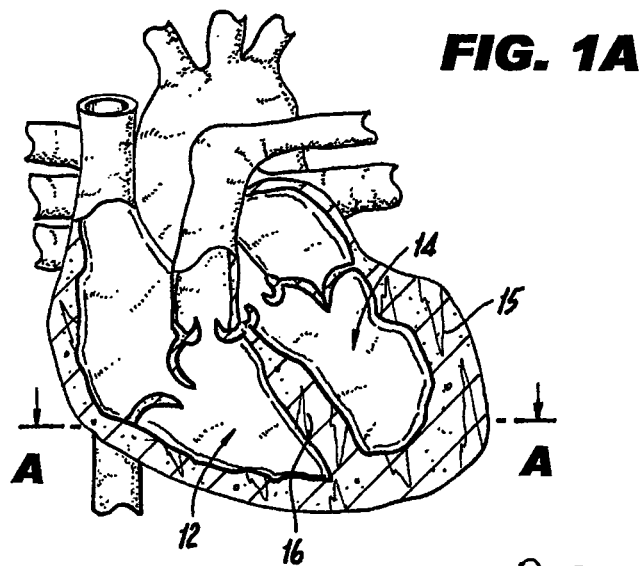
FIG. 1A is a schematic illustration of a mammalian heart.
Figure 1B:
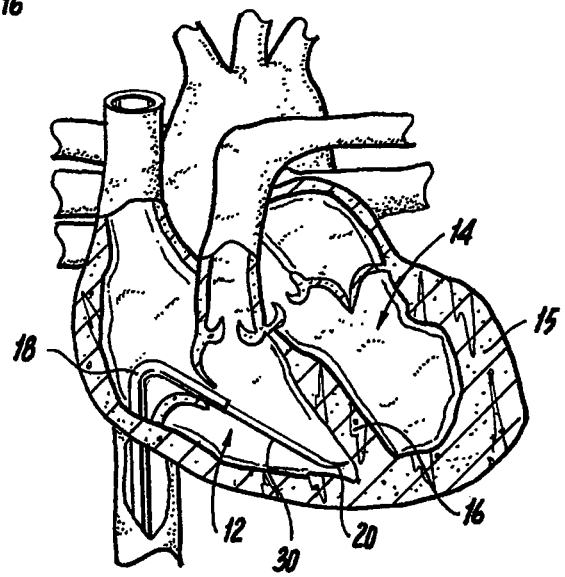
FIG. 1B is a schematic showing a sensing catheter that detects the infracted tissue and distinguishes the viable tissue before puncturing the septum and realigning the apex and reducing left ventricular volume.
Figure 1C:
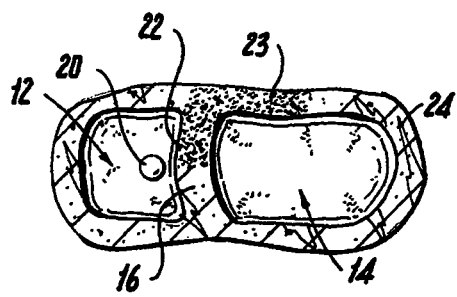
FIG. 1C illustrates a cross-section of a heart viewed along line A-A in FIG. 1A.
Figure 2A:
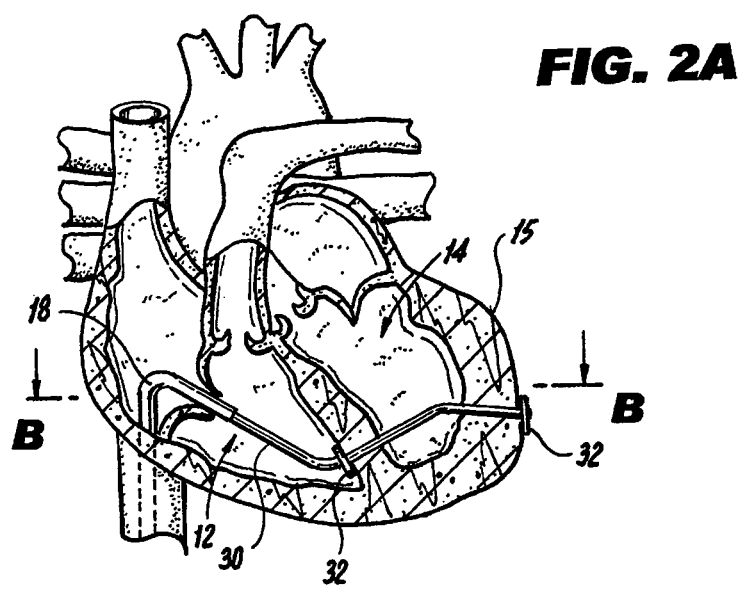
FIG. 2A is a schematic illustration of the use of a suturing device that is used to exclude the infarcted tissue and resulting volume reduction in the left ventricle.
Figure 2B:
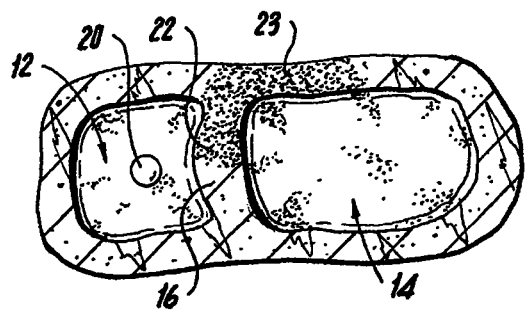
FIG. 2B illustrates a cross-section of a heart viewed along line B-B in FIG. 2A.
Figure 2C:
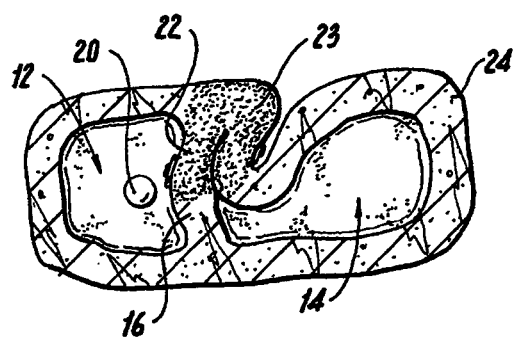
FIG. 2C illustrates a cross-section of a heart viewed along line B-B in FIG. 2A and showing the resizing of the ventricle.

FIG. 1A illustrates a mammalian heart 10 and identifies the right ventricle 12, left ventricle 14, left ventricle wall 15 and septum 16. Right ventricle 12 may also be referred to interchangeably herein and in the figures as "RV". Left ventricle 14 may also be referred to interchangeably herein and in the figures as "LV". Additionally, left ventricle 14 is also referred to herein as "left ventricle chamber."

FIGS. 1A-1C and 2A-2C illustrate a method of percutaneously accomplishing left ventricular restoration ("LVR"). In accordance with this method, a catheter 18 with a sensing element 20 is threaded through the femoral vein (not shown) into the right ventricle 12 of heart 10. It is to be understood that the invention is not limited to insertion of catheter 18 via the femoral vein and catheter 18 may be inserted via other arteries or veins. The sensing element 20 locates the infarcted tissue 22 of the interventricular septum 16. A commercially available device (EP Technologies, CA) that has the capability of discerning viable tissue from scar tissue could be used for the sensing purpose. This device operates on the concept of "monophasic action potential" ("MAP") and allows the operator to determine whether or not the site in contact with the sensing element has the desired properties.

Upon identifying this infarcted tissue, the physician threads the catheter 18 into the left ventricle 14 by advancing a perforating member 30 via a puncture through the tissue so identified in the septum 16. Perforating member 30 may be coextensive with catheter 18 or be fed through catheter 18. Advancing perforating member 30 can also be accomplished by using a retractable pointed element that is disposed at the distal tip of catheter 18. Alternatively, the catheter could be advanced over a steerable, sharp member that separately perforates the infarcted tissue of the septum. Once catheter 18 is in the left ventricle 14, the sensing element 20 is again used to confirm the location of additional infarcted tissue 23 in the left ventricular wall 24. Upon locating the infarcted tissue on the left ventricular wall, the physician advances the perforating member 30 through the tissue so identified until perforating member 30 is external to the ventricle and visible through the epicardium. The perforating member 30 shall then either be fixed on the surface of the heart with a disc or similar fixation member 32, or used to pull or retract additional fixation members or another grasping device, such as a suture (not shown), back through the free wall to the epicardium to the endocardium. Fixation member 32 is typically part of the catheter that is activated by maneuvering or activating something on the catheter In the former case, perforating member 30, affixed via fixation member 32 to left ventricle wall 15 is withdrawn through the free ventricular wall, back through the dilated left ventricle chamber 14 and back through the septum 16 at the site of the original perforation. As the perforating element 30 is further withdrawn, it will reduce the position of the free wall until that wall becomes contiguous with the septum 16 (or nearly so). Thus, the short axis of the left ventricle 14 is diminished by the extent to which the septum and free LV wall are apposed.

The catheters used for the percutaneous LVR in accordance with the present invention may be steerable/maneuverable catheters as are commonly used in surgical procedures. Suturing devices used in the alternative iterations could be commonly used sutures such as Prolene™, or could be made of shape memory alloys, such as Nitinol™.

The above steps could be accomplished using the following steps and devices:

1. Continuous direct and non-invasive visualization of the process using endoscopy, echocardiography, or other known non-invasive methods.

2. Multiple (assuming one will not be adequate to accomplish the restoration) perforating elements with multiple epicardial "discs" or other dispersing or fixation members, which are pulled together simultaneously to reduce the volume of the left ventricle.

3. A counter, externally compressive maneuver to ensure even reduction of the ventricle with balance movement of each of the multiple discs and evagination of the intervening scar as the reduction is carried out.

4. Fixation of the penetrating members on the right side if the interventricular septum to cement the reduction. Expanding discs, slats, or other fixation members to distribute the forces over a large area will be used.

5. The bulk of the device, not the portions of the penetrating members between the free wall discs and the RV septal discs, will be removed from the vascular system. As such, only a remnant, or detachable portion of the members that traversed the septum, LV, and free wall will remain, fixed at both ends with elements that distribute tension over a substantial area to ensure durability. These detachable elements will be a short segment, since the perforated portion will have been shortened as the walls are brought in closer approximation.

6. Alternatively, the leading edge of the fixation member shall have a retention element, such that the leading edge of the fixation member is retained on the epicardium. Once the leading edge is in place, the catheter is retracted through the puncture that was previously made through the infarcted septum. The retraction of the catheter now leaves the fixation member bridging the wall of the left ventricle and the septum. The trailing edge of the fixation member shall also have a retention element such that the trailing edge of the retention element is on the septum facing the right ventricle. The objective here is to bring together the infarcted tissues of the septum and the left ventricular wall together such that the left ventricular volume is reduced to an appropriate size and shape for a congestive heart failure patient to recover the desired ejection fraction of the heart. With the leading and trailing edge retention devices on the epicardium and the septum, respectively, pulling them away from each other would bring the two walls together and thus result in a reduced volume of the left ventricle. The two walls could also be brought together using suturing devices that are well known in the art.

Figure 3:
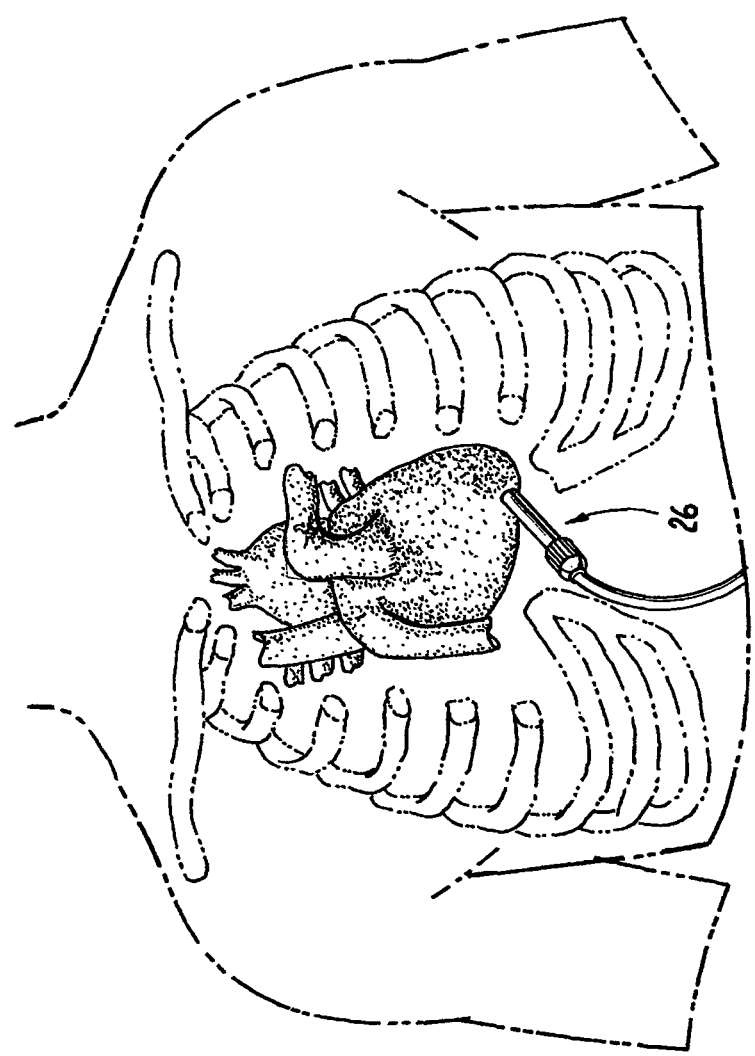
FIG. 3 illustrates the manner of direct visualization of the infarcted wall of the left ventricle and guiding the placement of the suture on the left ventricle during LVR.

FIG. 3 illustrates a bimanual strategy to achieve left ventricular restoration. In order to create a bimanual strategy, a direct visualization method from sub-xiphoid or trans-thoracic port access is used to determine the appropriate location of the penetration by the fixation member 32 (not shown in FIG. 3) through the endocardium of the left ventricular wall. An incision is typically made in the patient's chest into which a camera or video device 26 is inserted to provide visualization of the ventricle wall. This element may he used either alone or in combination with other visualization techniques.

Figure 4A:
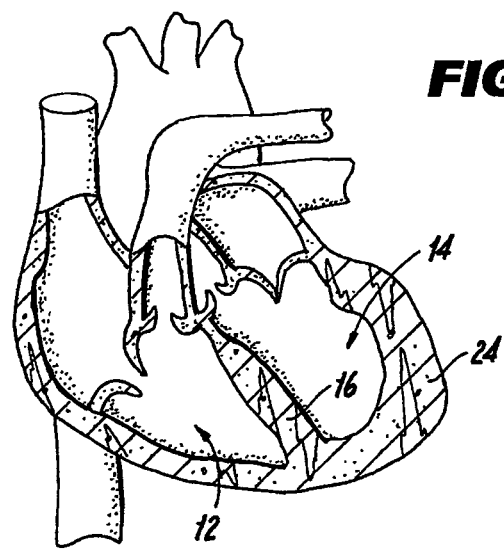
FIGS. 4A through 4F illustrate the step-by-step procedure for one embodiment of a percutaneous LVR procedure.
Figure 4B:
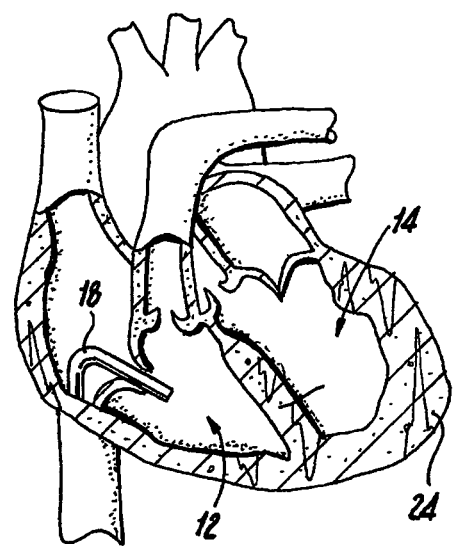

The procedure according to one embodiment of the present invention is shown in FIGS. 4A-4F which illustrate vertical cross-section views of heart 10. FIG. 4B is a vertical cross-sectional view of the heart showing a delivery catheter 18 inserted endovascularly into the right ventricle 12 according to an aspect of the present invention. Catheter 18 will be used to sense infarcted tissue, to be excluded, on the wall of septum 16, and to puncture across the septum wall to the left ventricle.

Figure 4C:
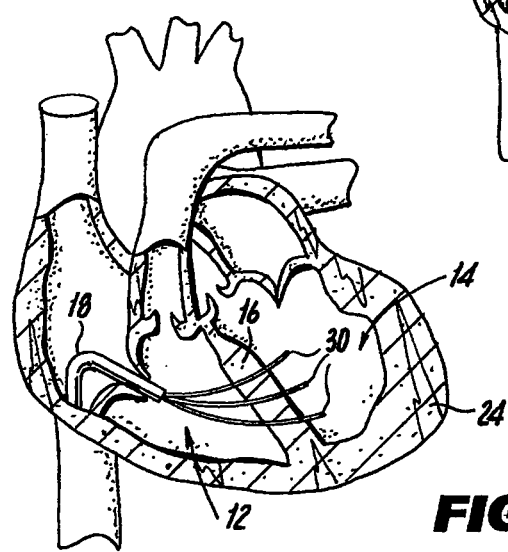
Figure 4D:
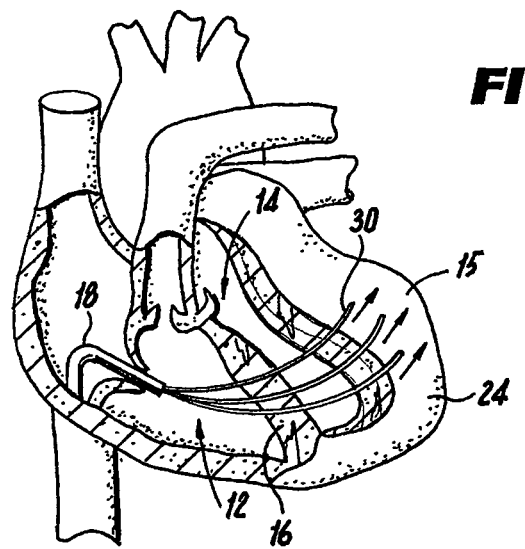

FIGS. 4C and 4D illustrate a guide wire or perforating element (shown as 30 in FIG. 1B) from the catheter of FIG. 4B through the septum wall, across the left ventricular chamber and into the free wall 15 of left ventricle 14 according to an aspect of the present invention.

Figure 4E:
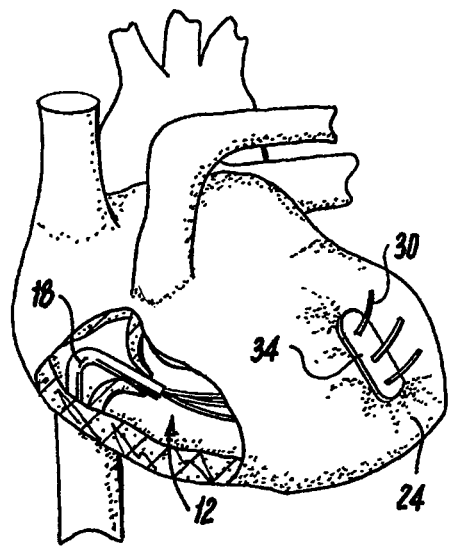

FIG. 4E illustrates the insertion of a retention element or member 34 into the delivery catheter 18 of FIG. 4D for placement of the tension member outside the free wall with respect for the left ventricle to reduce left ventricular volume according to an aspect of the present invention. Retention element 34 may be a collar, a hook, a barb, a fastener or a clip but the invention is not limited in this respect.

Figure 4F:
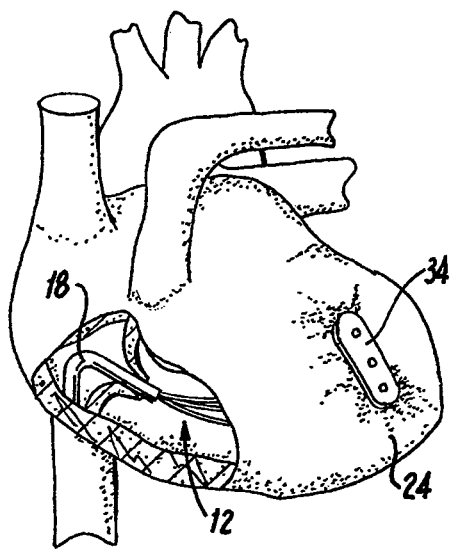

FIG. 4F shows the retention element 34 at the end of the procedure to exclude infarcted or scarred tissues, hence reduce the ventricular volume.

Figure 5:
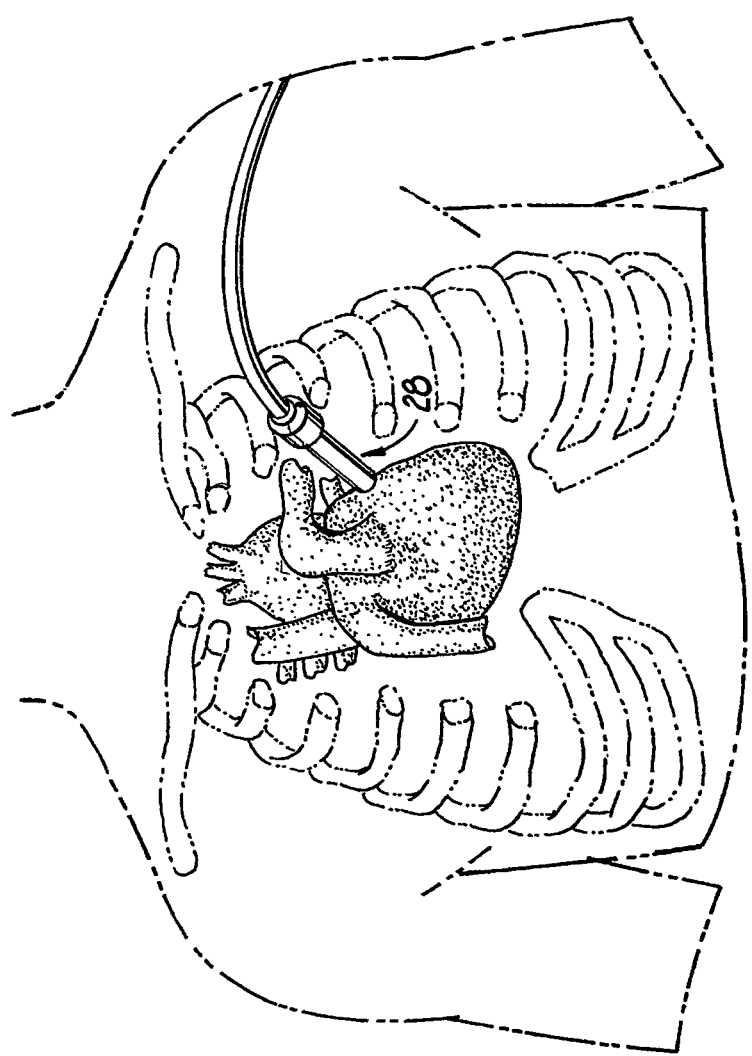
FIG. 5 shows a thoracoscopic suction and suturing device that could be used for LVR.

In another embodiment, the procedure utilizes a thoracoscopic surgical approach, i.e., synching the infarcted tissue from the epicardial side as opposed to the endocardial approach described under the percutaneous procedure. FIG. 5 illustrates the use of thoracoscope 28 in this approach. In this iteration, excess portions of the perforating members would be removed after the free wall was reduced and a force dispersing member (not shown) attached.

Figure 6A:
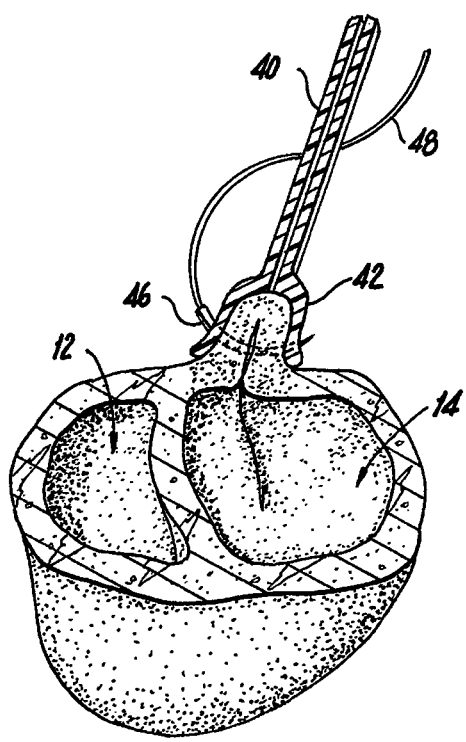
FIGS. 6A and 6B illustrate an epicardial or thorascopic approach to accomplish LVR.
Figure 6B:
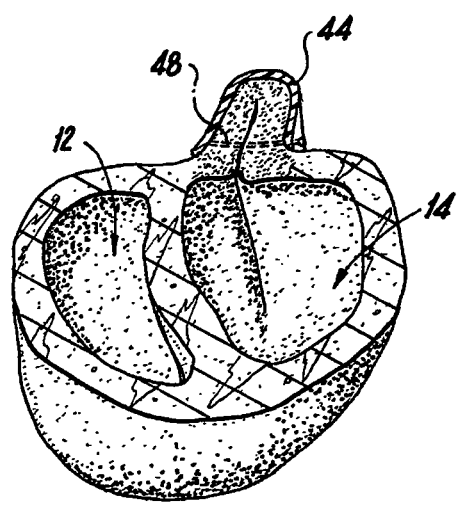

FIG. 6A illustrates a suction device 40 used to form a dilated left ventricle wall as part of an off-pump epicardial thoracoscopy procedure. Suction device 40 may incorporate a clamp element 42 and a patch 44, which can be made of woven Dacron or extracellular matrix, but is not limited in this regard. After left ventricle 14 is dilated using suction device 40, clamp 42 is applied which brings the walls of the left ventricle 14 together and thus re-sizes the left ventricle 14 to provide decreased heart wall tension and improved ejection fraction. Patch 44 is applied over the clamped portion of the left ventricle. A closure device 46 then provides stitches 48 along the clamped section as illustrated in FIG. 6B.

Figure 7A:
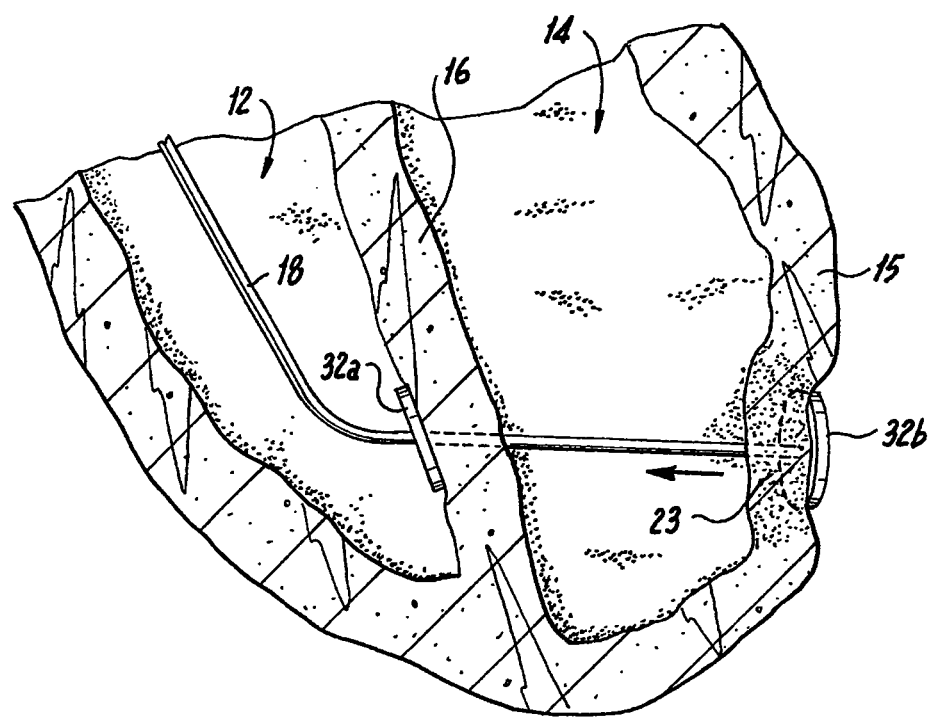

FIGS. 7A through 7D further illustrate the different device embodiments that could be used for percutaneous LVR. FIG. 7A of the procedure illustrated in FIG. 4C-E, where distal and proximal elements are used to bring the free wall of the left ventricle 14 to be in contact with the wall of septum 16. FIG. 7A is a vertical cross-sectional view of the heart showing a delivery catheter 18 with a curved distal tip inserted into the right ventricle 12 proximate the wall of septum 16 for delivering a tension member or fixation member assembly according to an aspect of the present invention.

Figure 7B:
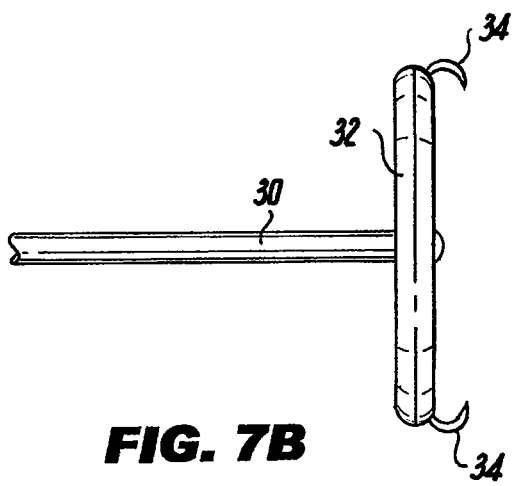

Delivery catheter 18, which may also could act as a sensing catheter (such as 30 in FIG. 1B) or contain a tissue-viability-sensing element, is introduced into the right ventricle 12. Upon penetrating the septum and then identifying the infarct area 23 on the left ventricular wall 15, a distal fixation element 32a is deployed to be embedded in the infarct area 23. As catheter 18 is withdrawn through septum 16, a proximal fixation element 32b is deployed to be in contact with the septum 16. The withdrawal of the catheter 18 and the fact that distal fixation element 32a is embedded in the left ventricular wall brings the left ventricular wall closer to the septum 16 and thereby decreases the ventricular volume. Proximal and distal fixation elements 32a, 32b may be disk shaped and may be made of biocompatible materials. Proximal and distal fixation elements 32a, 32b may be provided with one or more retention elements 34 as shown in FIG. 7B. Retention element 34 could be a collar, hook, barb, fastener or a clip to facilitate and secure proximal and distal fixation elements in the appropriate position. These elements could also made of biological materials. Proximal and distal fixation elements 32a, 32b may also be impregnated or loaded with angiogenic factors, drugs, gene-regulated viral vectors, cellular materials, or other substances such that they could promote desired responses.

FIG. 7C illustrates the location of the distal and proximal fixation elements 32a, 32b prior to the ventricle resizing procedure, where they are spaced apart. FIG. 7D illustrates the end of the procedure, wherein by pulling or retracting perforating element 30 between the distal and proximal fixation elements 32a, 32b away from the left ventricular wall, the septum and the left ventricular wall are brought closer and thereby reduce the volume of the left ventricle. The proximal and distal fixation elements 32a, 32b could also be used in a thoracoscopic procedure, where instead of connector being pulled away from the distal element, the connector is now pulled away from the proximal element.

The proximal and distal fixation elements 32a, 32b could also be made of two sub-elements as shown in FIG. 7E. Proximal retaining element 32a may comprise first septum sub-element 36a and second septum sub-element 36b positioned on both side of septum 16. Additionally, distal retaining element 32b, may comprise first left ventricle sub-element 38a and second left ventricle sub-element 38b positioned on both side of left ventricle wall. Such a two-piece structure for the proximal and distal elements would also support the weakened infarcted tissue at the septum and the left ventricular wall.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for reducing left ventricular volume in a congestive heart failure heart, the heart having a left ventricle, the method comprising the steps of:
   a. identifying infarcted tissue during open chest surgery;
   b. dilating said ventricle by applying suction to an epicardium of said ventricle;
   c. reducing the left ventricle volume by clamping of the dilated portion of said ventricle so as to bring walls of the left ventricle together;
   d. securing the clamped portion by stitching along the clamped portion with the stitching penetrating through the clamped walls to affix the walls of said ventricle together to achieve appropriate functional contractile geometry of said ventricle.

2. The method of claim 1, wherein said method comprises a minimally invasive surgery.

3. The method of claim 1, further comprising the step of sensing the infarcted tissue.

4. The method of claim 3, wherein the infarcted tissue is the myocardium.

5. The method of claim 1, further comprising realigning a ventricular apex by altering the geometry of the ventricle and decreasing wall tension.

6. The method of claim 3, wherein the step of sensing the infarcted tissue may be performed by a procedure selected from the group consisting of: pacing, angiography, echocardiography, and tissue Doppler.

7. The method of claim 1, further comprising introducing a thoracoscope or camera into an incision to facilitate visualization of the epicardium during reducing of the left ventricle volume.

8. The method of claim 1, wherein securing the clamped portion further comprises the step of applying a patch on said dilated portion.

9. The method of claim 1, wherein the applying of suction comprises engaging an epicardium of the left ventricle with a suction device under thoracoscopic guidance so that the epicardium is drawn into the suction device and inner surfaces of the wall of the left ventricle are brought together.

10. The method of claim 8, wherein applying the patch comprises applying a woven material or an extracellular matrix along an epicardium of the left ventricle.

* * * * *